United States Patent
Zheng et al.

(10) Patent No.: US 6,447,460 B1
(45) Date of Patent: Sep. 10, 2002

(54) METHOD FOR AUTOMATED EXCLUSION OF DEEP VENOUS THROMBOSIS

(75) Inventors: X. Lu Zheng; Tianning Xu; David M. Tumey, all of San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 0 days.

(21) Appl. No.: 09/286,190

(22) Filed: Apr. 5, 1999

Related U.S. Application Data

(60) Provisional application No. 60/111,479, filed on Dec. 9, 1998.

(51) Int. Cl.[7] .................................................. A61B 5/00
(52) U.S. Cl. ........................ 600/549; 600/481; 600/504
(58) Field of Search ................................ 600/473, 474, 600/481, 482, 485, 504, 507, 408, 549, 555; 128/920, 925; 374/100, 112

(56) References Cited

U.S. PATENT DOCUMENTS

| | | | | |
|---|---|---|---|---|
| 4,310,003 A | | 1/1982 | Schlager | 128/736 |
| 4,379,461 A | | 4/1983 | Nilsson et al. | 128/736 |
| 4,416,552 A | | 11/1983 | Hessemer et al. | 374/117 |
| 4,445,516 A | | 5/1984 | Wollnik et al. | 128/736 |
| 4,494,550 A | | 1/1985 | Blazek et al. | 128/664 |
| 4,574,812 A | | 3/1986 | Arkans | 128/691 |
| 4,721,113 A | | 1/1988 | Stewart et al. | 128/661 |
| 4,849,885 A | | 7/1989 | Stillwagon et al. | 364/413 |
| 4,920,973 A | | 5/1990 | Tanaka et al. | 128/736 |
| 5,090,417 A | | 2/1992 | Mollan et al. | 128/691 |
| 5,205,293 A | * | 4/1993 | Ito et al. | 600/549 |
| 5,282,467 A | | 2/1994 | Piantadosi et al. | 128/633 |
| 5,546,955 A | | 8/1996 | Wilk | 128/736 |
| 5,596,995 A | * | 1/1997 | Sherman et al. | 600/549 |
| 5,637,871 A | | 6/1997 | Piety et al. | 250/330 |
| 5,924,997 A | * | 7/1999 | Campbell | 600/549 |
| 5,935,075 A | * | 8/1999 | Casscells et al. | 600/549 |
| 5,991,654 A | * | 11/1999 | Tumey et al. | 600/473 |

OTHER PUBLICATIONS

Stemmer, Robert B. et al., Light Reflection Rheography and the Diagnosis of Thrombosis in the Deep Leg Veins, Mar. 1984, pp. 69–71.

* cited by examiner

*Primary Examiner*—Cary O'Connor
*Assistant Examiner*—Charles Marmor, II

(57) ABSTRACT

An automated screening tool for the exclusion of deep venous thrombosis generally comprises a sensor array for gathering thermal data from the lower limbs of a patient suspected of DVT; a processor for automated analysis of the gathered data; and a display device for reporting the exclusion or non-exclusion of DVT. In the preferred embodiment of the present invention, a microprocessor based system is utilized to control the gathering of thermal data and, thereafter, the reporting of the gathered data to the processor. According to the preferred method for use of the present invention, the gathered thermal data is utilized, alone or in combination with other indicators, as a factor for exclusion of DVT based upon an implemented algorithm.

According to the preferred embodiment of the present invention, a neural network or genetic algorithm is implemented within the processor in order to make an entirely objective determination relative the presence of DVT. This feature makes the present invention particularly adapted to multiple risk factor analysis, wherein factors such as calf circumference; positive Homan sign; colorimetry reading of the limbs; recent surgery or trauma; history of DVT, phlebitic syndrome or venous insufficiency; or presently uncannulated veins may be considered along with thermographic data.

20 Claims, 5 Drawing Sheets

METHOD FOR AUTOMATED EXCLUSION OF DEEP VENOUS THROMBOSIS

RELATED APPLICATION

The present invention claims, under 35 USC §119(e), all available benefit of the filing of U.S. provisional patent application Ser. No. 60/111,479 filed Dec. 9, 1998. By this reference, the full disclosure, including the drawings, of U.S. provisional patent application Ser. No. 60/111,479 is incorporated herein as though now set forth in its entirety.

FIELD OF THE INVENTION

The present invention relates to the diagnosis of deep venous thrombosis. More particularly, the invention relates to a high-sensitivity method and automated apparatus for the noninvasive exclusion of acute, proximal deep venous thrombosis in a significant percentage of those patients suspected of, but actually negative for, deep venous thrombosis.

BACKGROUND OF THE INVENTION

Deep venous thrombosis (DVT) is a well-known clinical indication commonly occurring in post-operative patients, elderly persons and patients with severe debilitating illness or malignant diseases, especially malignancy of the pelvis or abdomen. It is a frequent cause of emergency admission to hospital and, particularly in the case of acute, proximal DVT, can result in pulmonary embolism (PE), which is often fatal. The treatment of DVT is known to most often involve the administration of anticoagulant therapy, which presents the risk of hemorrhage and, in pregnant women, poses hazard to the viability of the fetus. Consequently, it is generally accepted standard of care to obtain a reliable confirmation of DVT prior to beginning treatment.

In present investigative practice, venography is accepted as the gold standard for the clinical confirmation of DVT. Unfortunately, venography is invasive, involves the injection of radiographic contrast media and exposes the patient to ionizing radiation during the examination. While each of these factors militates away from the unnecessary utilization of venography, the injection of radiographic contrast media is of particular concern. These media are known for potentially fatal complications including anaphylaxis or anaphylactic reaction, bronchospasm, angioneurotic edema with laryngeal spasm or edema, severe hypotension with circulatory failure and cardiac arrhythmias or arrest. In addition, the physical injection of the contrast media poses the risk of actually causing a DVT to break loose, resulting in PE. In order to avoid the attendant risks of venography, Doppler ultrasound has been employed where available as a screening tool for the confirmation of some DVT, thereby eliminating the need for a percentage of venography examinations.

Unfortunately, Doppler ultrasound is operator dependent and somewhat subjective in interpretation. As a result, Doppler is not generally regarded as reliable for the exclusion of DVT. Therefore, in the case of negative Doppler results, it is still necessary to perform venography for the exclusion of DVT. To compound this deficiency, Doppler equipment and trained operators are not readily available and where available are in very high demand. Recognizing the hazards of venography and the limitations of Doppler, researchers have recently focused effort on the development of efficient screening means for the exclusion of DVT. The general theory is that if a percentage of patients suspected of DVT can be reliably excluded from the indication then more Doppler resources will be available for the confirmation of DVT. The desired net result is that venography will only be necessary in that percentage of cases that cannot be reliably excluded or confirmed by other available means.

From these efforts, thermography and, in particular, infrared (IR) imaging has emerged as a promising technique, offering the advantages of high sensitivity and relative low cost through a noninvasive method. In general, thermography involves the thermal mapping of the suspected DVT positive patient's lower extremity and evaluation of the resulting thermogram for known indications, or more precisely the lack thereof, of DVT. The method relies primarily on two known observables. First, the thermogram obtained from a DVT negative subject will exhibit a generally smooth temperature gradient of approximately 3° C. between the upper thigh and the lower calf. Second, there is no significant contralateral asymmetry in the thermograms of a DVT negative subject's lower limbs. In other words, the left and right thermograms are thermally similar in posterior or anterior view. By contrast, the thermogram of a DVT affected subject's lower limb will lack a smooth temperature gradient and, because it is unlikely that both limbs will be positive at the same time, will likely exhibit temperature readings higher than those of the other limb.

It should be noted that, while the process of obtaining a thermogram is largely objective and operator independent, the process of interpreting a thermogram image for the exclusion of DVT is largely subjective, comparable to a physician's reading of an X-ray. It is therefore a primary object of the present invention to provide a method and apparatus whereby the evaluation of the patient for exclusion of DVT is made entirely objective through automated processing of objectively obtained data.

Although much less expensive than either Doppler ultrasound or venography, thermography typically involves the use of a relatively expensive infrared camera for obtaining the thermogram image. With modern constraints dictating ever more judicious usage of the healthcare dollar, it is necessary to take every opportunity to reduce the cost of patient care while maintaining or exceeding established standard of care. It is therefore another object of the present invention to provide a method and apparatus whereby the cost associated with the exclusion of DVT is reduced without sacrifice in diagnostic reliability.

It is a further object of the present invention to capitalize upon the automated features introduced therewith to increase diagnostic reliability by providing a method and apparatus adaptable for multiple risk factor and/or dynamic analysis.

It is yet another object of the present invention to promote increased patient care by providing a method and apparatus that makes use of disposable components, thereby reducing the risk associated with patient contaminants.

Finally, it is an object of the present invention to provide a method for automated analysis of thermographic data that is useful not only in the apparatus of the present invention but is also extendable for use in the objective analysis of traditionally obtained thermogram images, including those obtained through IR imaging.

SUMMARY OF THE INVENTION

In accordance with the foregoing objects, the present invention—an automated screening tool for the exclusion of deep venous thrombosis—generally comprises a sensor array for gathering of thermal data from the lower limbs of a patient suspected of DVT; a processor for automated analysis of the gathered data; and a display device for reporting the exclusion or non-exclusion of DVT. In the preferred embodiment of the present invention, a microprocessor based system is utilized to control the gathering of thermal data and, thereafter, the reporting of the gathered data to the processor. According to the preferred method for use of the present invention, the gathered thermal data is utilized, alone or in combination with other indicators, as a factor for exclusion of DVT based upon an implemented algorithm.

According to the preferred embodiment of the present invention, a neural network or genetic algorithm is implemented within the processor in order to make an entirely objective determination relative the presence of DVT. This feature makes the present invention particularly adapted to multiple risk factor analysis, wherein factors such as calf circumference; positive Homan sign; colorimetry reading of the limbs; recent surgery or trauma; history of DVT, phlebitic syndrome or venous insufficiency; or presently uncannulated veins may be considered along with thermographic data.

Finally, many other features, objects and advantages of the present invention will be apparent to those of ordinary skill in the relevant arts, especially in light of the foregoing discussions and the following drawings and exemplary detailed description.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 1:
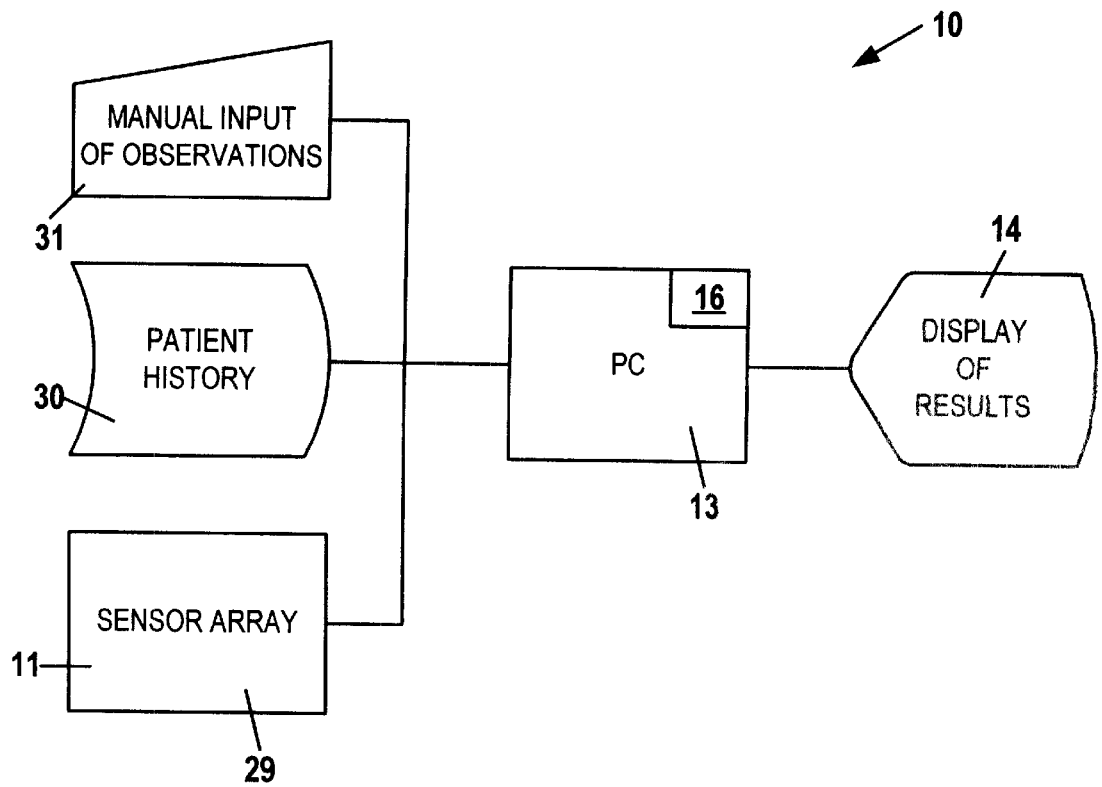
FIG. 1 shows, in schematic block diagram, the preferred implementation of the present invention 10.

Referring to the various figures and FIG. 1 in particular, the present invention 10 generally comprises a sensor array 11 for gathering of thermal data from the lower limbs 12 of a patient suspected of DVT; a processor 13 for automated analysis of the gathered data; and a display device 14 for reporting the exclusion or non-exclusion of DVT. In the preferred embodiment of the present invention 10, a microprocessor based system 15 is utilized to control the gathering of thermal data and, thereafter, the reporting of the gathered data to the processor 13. According to the preferred method for use of the present invention 10, the gathered thermal data is utilized, alone or in combination with other indicators, as a factor for exclusion of DVT based upon an implemented algorithm 16.

Figure 2:
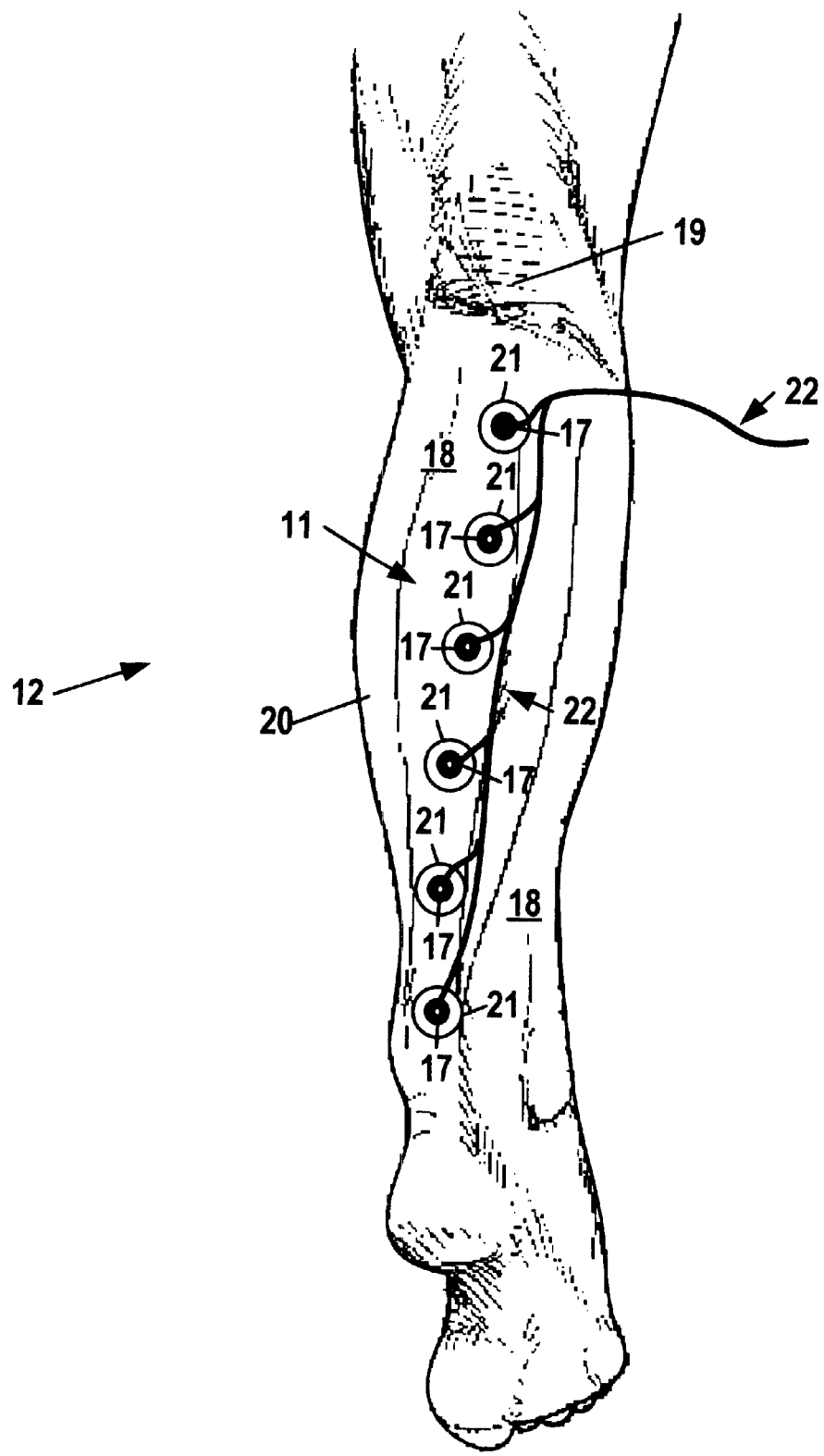
FIG. 2 shows, in elevational view, the sensor array 11 of the present invention 10 as applied to the posterior surface 18 of a patient's lower limb 12.
Figure 3:
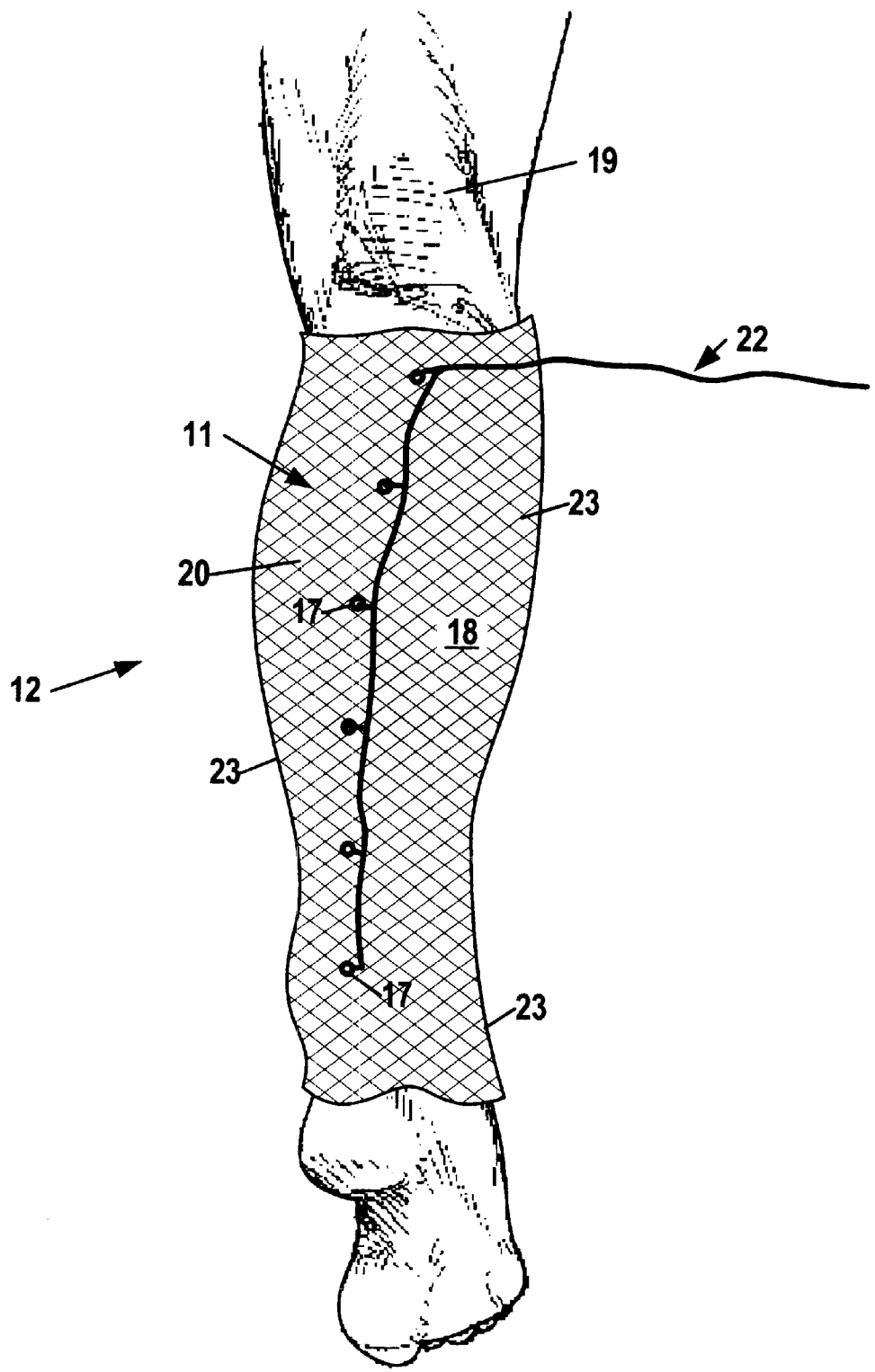
FIG. 3 shows, in elevational view, an alternative arrangement for attachment of the sensor array 11 of the present invention 10 to the posterior surface 18 of a patient's lower limb 12.

As particularly shown in FIG. 2, thermal data is collected through a plurality of sensors disposed on the posterior surface 18 of the suspected patient's lower thigh 19 and calf 20. In the preferred embodiment of the present invention 10, these sensors 17 comprise thermistors, which may be attached as shown with patches 21 of medical grade adhesive tape. Spacing between the sensors 17 may be controlled as shown through their predetermined disposition along a provided electrical harness 22. Alternatively, and as shown in FIG. 3, a mesh or other type stocking 23 may be pre-fitted with the sensors 17 for application over the patient's lower limb 12. It should be noted that although the preferred embodiment comprises thermistors, other substantially equivalent components may be substituted within the realm of those of ordinary skill in the arts.

Figure 4:
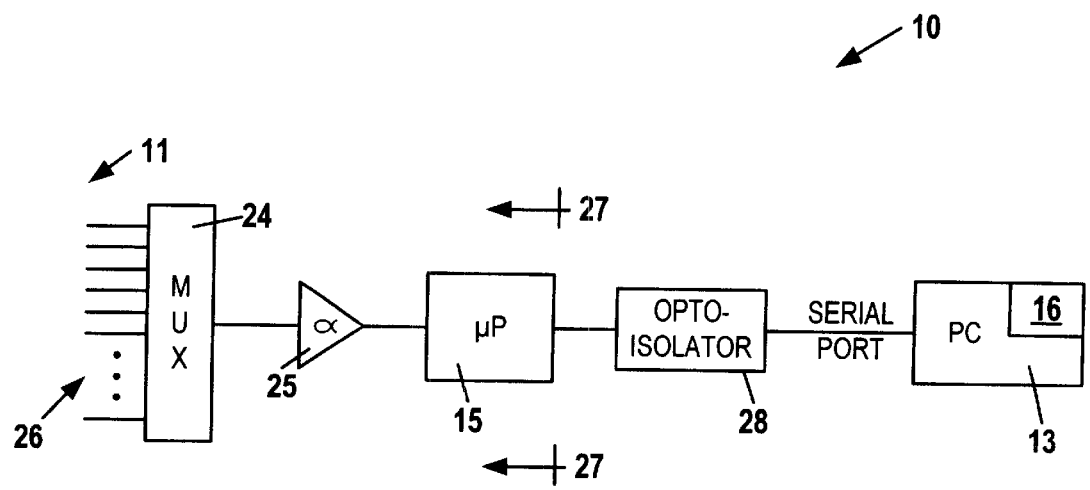
FIG. 4 shows, in schematic block diagram, details of the data acquisition portion 27 of the preferred embodiment of the present invention 10.

As shown in FIG. 4, the sensors 17 are in electrical communication with a microprocessor based control circuit 15 through an interposed analog multiplexor 24 and single amplifier channel 25. This arrangement allows acquisition of the analog sensor data 29 without introduction of error due to amplifier gain variances and without the need for precisely calibrated acquisition hardware. In the preferred embodiment of the present invention 10, up to sixteen channels 26 are utilized to take temperature readings from up to eight points along the posterior region 18 of each of the patient's lower limbs 12. Although capability is provided for this number of readings, it should be noted that empirical results indicate that as few as four points per leg may suffice and in the figures only six sensors 17 are shown.

The microprocessor based circuit 15 converts each analog temperature reading to a digital signal, which is then serially transmitted to the PC based processor 13. Because the sensors 17 bring the patient into close proximity with an electrical device, it is preferred that the PC based processor 13 be electrically isolated from the acquisition portion 27 of the invention 10. In the preferred embodiment of the present invention 10, an opto-isolator 28 is utilized to this end. The objective analysis portion of the present invention is then implemented in software 16 within the PC based processor 13.

Referring back to FIG. 1, it is again noted that the implemented algorithm 16 may make the objective determination on the basis of the sensor data 29 alone or in combination with patient history data 30 or manually input present observations 31. In the latter case, the present invention 10 may be considered a multiple risk factor analysis system, particularly adapted to consider such factors as calf circumference; positive Homan sign; colorimetry reading of the limbs; recent surgery or trauma; history of DVT, phlebitic syndrome or venous insufficiency; or presently uncannulated veins, among other possible factors. After processing, as will be better understood further herein, the exclusion or non-exclusion of DVT may be displayed through the processor's monitor 14 or other desired output device.

In carrying out the present invention 10, an intelligent algorithm 16 is implemented within the PC based processor 13. This algorithm, which may be a neural network, genetic algorithm or other ruled based algorithm, is adapted to automatically analyze the collected thermal data 29 for the exclusion of DVT based upon the known principles of thermography, as previously discussed herein. The implementation of a neural network or genetic algorithm, however, enables an entirely objective analysis thereby eliminating the need for special training in the reading of thermographic imagery. Additionally, these algorithms allow the automated consideration of multiple risk factors 29, 30, 31—a feature virtually impossible with prior art methods due to the inability to subjectively assign proper weight to each of the many factors.

Because the present invention 10 is primarily intended as an automated screening tool for the exclusion of DVT, it is important to note that in implementation of the algorithm 16 it is possible to bias the result for increased patient safety. For example, while training a neural network the implementing engineer can penalize the system more for incorrectly excluding a present DVT than for incorrectly failing to exclude a non-present DVT. This may be regarded as giving the algorithm 16 a conscience, through which the sensitivity of the tool 10 may be made very high.

Figure 5:
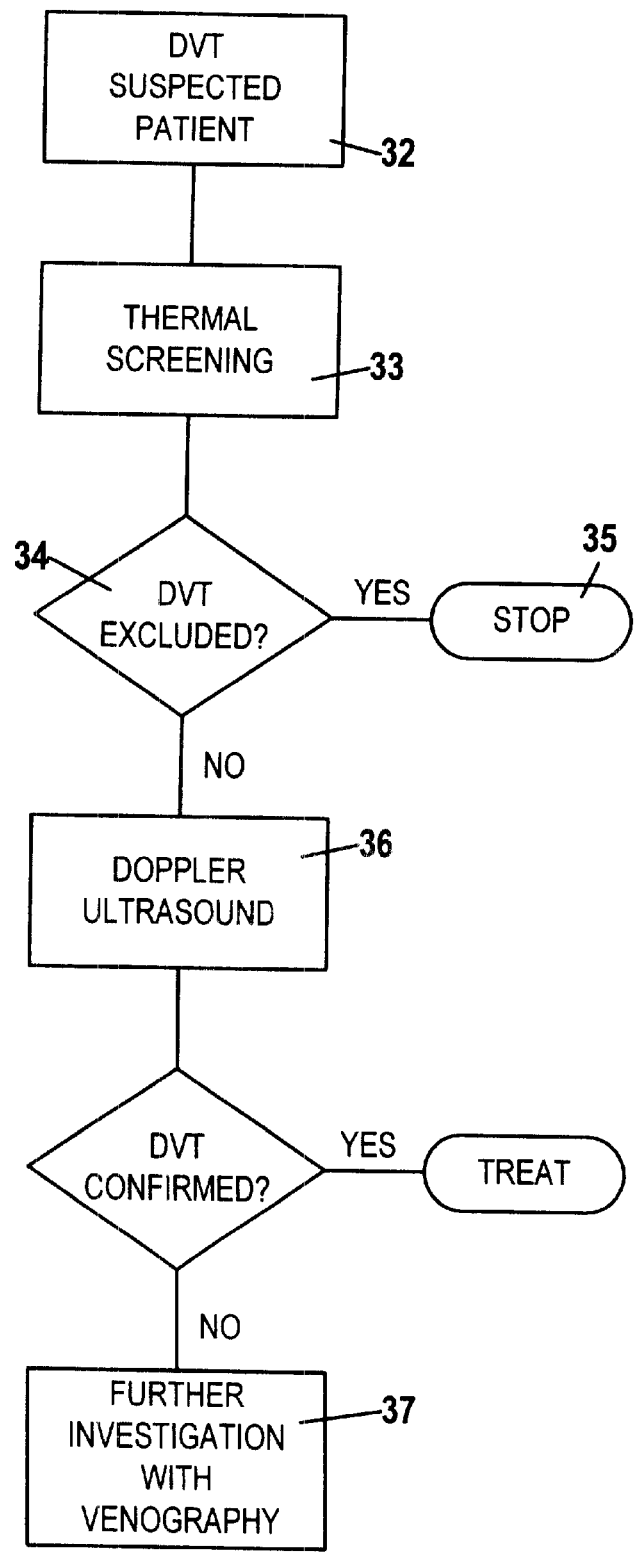
FIG. 5 shows, in flowchart, the intended utilization for the present invention 10.

Referring to FIG. 5, the intended application of the present invention 10 is now shown. In clinical practice, the DVT suspected patient is, once identified, submitted for further investigation 32. The present invention 10 serves as the starting point for that investigation by providing a highly reliable, but readily available—both in terms of resources and per patient costs, means for excluding up to 30% of DVT suspected patients 33. If excluded, the investigation is terminated 35 without further expenditure of time or other resources 34.

It is noted, however, that if not excludable at this stage the patient must undergo further testing by Doppler ultrasound 36 and/or venography 37. This highlights the great demand for readily available and reliable means for the exclusion of DVT. It also emphasizes the importance of even the slightest improvement in available methods and/or apparatus.

While the foregoing description is exemplary of the preferred embodiment of the present invention 10, those of ordinary skill in the relevant arts will recognize the many variations, alterations, modifications, substitutions and the like as are readily possible, especially in light of this description and the accompanying drawings. For example, utilization of a neural network or genetic algorithm enables dynamic analysis of sensor data, which in such an implementation would form a time series. This type of analysis not only reduces the need for a strictly temperature controlled environment and/or equilibrium of the lower limbs with the environment, but also allows for extension of the invention with a challenge appliance. Such an appliance may be a specially formed boot or leg wrap that is adapted to be heated or cooled with, for example, a circulated fluid. Although challenge techniques are known to those of ordinary skill in the art, Applicant knows of no implementation to date that is capable of objectively analyzing data taken during or immediately after a challenge event. In any case, because the scope of the present invention 10 is much broader than any particular embodiment, the foregoing detailed description should not be construed as a limitation of the scope of the present invention 10, which is limited only by the claims appended hereto.

What is claimed is:

1. A diagnostic method for the automated and objective exclusion of deep venous thrombosis (DVT) in a patient's limb, said diagnostic method comprising the steps of:

obtaining a sensed thermal characteristic of the patient's limb;

converting said thermal characteristic to a processor compatible format; and processing said format in an automated and objective analysis, said analysis being adapted to exclude the patient for DVT based upon said sensed thermal characteristic.

2. The diagnostic method as recited in claim 1, wherein said obtaining a sensed thermal characteristic step comprises using a thermistor to measure said thermal characteristic.

3. The diagnostic method as recited in claim 1, wherein said obtaining a sensed thermal characteristic step comprises using a plurality of thermistors to measure said thermal characteristic, said plurality of thermistors forming an array of sensors.

4. The diagnostic method as recited in claim 3, wherein said array of sensors is adapted for disposition along the posterior region of the patient's calf region.

5. The diagnostic method as recited in claim 4, wherein said array is adapted to dispose said sensors at predetermined intervals one to another.

6. The diagnostic method as recited in claim 5, wherein said array comprises a flexible strip, said sensors being disposed at predetermined positions along one side of said flexible strip and said one side being provided with an adhesive for application to the patient's calf.

7. The diagnostic method as recited in claim 3, wherein said converting said thermal characteristic step comprises using an acquisition device in independent communication with each said sensor, said acquisition device being adapted to convert said thermal characteristic measured by each said sensor to said processor compatible format.

8. The diagnostic method as recited in claim 7, wherein:
said acquisition device comprises an analog multiplexor and an amplifier; and
said acquisition device is adapted to independently amplify through said amplifier said thermal characteristic measured by each said sensor of said array.

9. The diagnostic method as recited in claim 7, wherein said acquisition device comprises a microprocessor, said microprocessor being adapted to control:
acquisition of said thermal characteristic;
conversion of said thermal characteristic to said processor compatible format; and
presentation of said format to a processor for said automated and objective analysis.

10. The diagnostic method as recited in claim 9, wherein said acquisition device further comprises:
an analog to digital converter for converting said thermal characteristic to said processor compatible format; and
a serial communication channel for transmission of said format to said processor, said serial communication channel comprising an opto-coupler adapted for electrical isolation of said acquisition device from said processor.

11. The diagnostic method as recited in claim 1, wherein said processing said format step comprises using a genetic algorithm to objectively determine whether said thermal characteristic indicates exclusion of the patient for DVT.

12. The diagnostic method as recited in claim 1, wherein said processing said format step comprises using a neural network to objectively determine whether said thermal characteristic indicates exclusion of the patient for DVT.

13. The diagnostic method as recited in claim 1, wherein said processing said format step comprises performing a multiple risk factor analysis.

14. The diagnostic method as recited in claim 13, wherein said performing a multiple risk factor analysis step comprises analyzing said format and at least one other indicator of DVT, said analyzing step being conducted in an entirely objective manner.

15. The diagnostic method as recited in claim 14, wherein said analyzing step comprises using a neural network for indicating exclusion of the patient for DVT.

16. The diagnostic method as recited in claim 15, wherein said neural network comprises a bias factor for patient safety.

17. The diagnostic method as recited in claim 13, wherein said performing a multiple risk factor analysis step comprises analyzing said format and a plurality of other indicators of DVT.

18. The diagnostic method as recited in claim 1, said diagnostic method further comprising reporting excludability of the patient for DVT.

19. The diagnostic method as recited in claim 18, wherein said reporting excludability step comprises displaying a result on a monitor.

20. The diagnostic method as recited in claim 18, wherein said reporting excludability step comprises recording computational data in a magnetic medium.

* * * * *